(12) United States Patent
Maahs

(10) Patent No.: US 6,440,120 B1
(45) Date of Patent: Aug. 27, 2002

(54) BENDABLE SHAPE-RETAINING CANNULA

(75) Inventor: Tracy D. Maahs, Redwood City, CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

(21) Appl. No.: 09/145,808

(22) Filed: Sep. 2, 1998

(51) Int. Cl.$^7$ .................. A61M 25/00; A61M 31/00; A61M 29/00

(52) U.S. Cl. ............... 604/523; 604/96.01; 604/264; 604/509; 606/194

(58) Field of Search .............. 604/523–25, 174, 604/264, 506–8, 96.01, 103, 103.06, 103.08, 103.11, 104, 118, 35, 509, 164.01, 164.04, 271, 532, 540, 279, 541; 138/118, 121, 137; 128/898; 606/200, 191, 194, 198; 607/122–25

(56) References Cited

U.S. PATENT DOCUMENTS

| | | | | |
|---|---|---|---|---|
| 2,625,934 A | * | 1/1953 | Halliday | |
| 3,459,175 A | * | 8/1969 | Miller | 604/96 |
| 3,874,388 A | * | 4/1975 | King et al. | 128/334 |
| 4,508,535 A | * | 4/1985 | Joh et al. | 604/174 |
| 4,593,690 A | * | 6/1986 | Sheridan e tal. | 604/523 |
| 4,610,661 A | * | 9/1986 | Possis et al. | 604/113 |
| 4,784,639 A | * | 11/1988 | Patel | 604/508 |
| 4,795,446 A | * | 1/1989 | Fecht | 604/264 |
| 5,058,934 A | * | 10/1991 | Brannon | 285/226 |
| 5,146,925 A | * | 9/1992 | Snow | |
| 5,192,286 A | * | 3/1993 | Phan et al. | 604/264 |
| 5,339,809 A | * | 8/1994 | Beck, Jr. et al. | 604/165 |
| 5,695,519 A | * | 12/1997 | Summers et al. | 606/200 |
| 5,715,818 A | * | 2/1998 | Swartz et al. | 604/523 |
| 5,769,816 A | * | 6/1998 | Barbut et al. | 604/96 |
| 5,827,324 A | * | 10/1998 | Cassell et al. | 606/200 |
| 5,895,399 A | * | 4/1999 | Barbut et al. | 606/159 |
| 5,980,503 A | * | 11/1999 | Chin | 604/509 |
| 6,019,753 A | * | 2/2000 | Pagan | 604/523 |
| 6,021,816 A | * | 2/2000 | Jeltsch et al. | 138/121 |
| 6,053,932 A | * | 4/2000 | Daniel et al. | 606/200 |
| 6,146,400 A | * | 11/2000 | Hahnen | 606/185 |

* cited by examiner

Primary Examiner—Angela D. Sykes
Assistant Examiner—P. M. Bianco
(74) Attorney, Agent, or Firm—Lyon & Lyon LLP

(57) ABSTRACT

A bendable shape-retaining cannula and methods of use. The bendable shape-retaining cannula comprises a tubular member having a proximal region, a distal region adapted to enter a blood vessel or heart chamber, a lumen therebetween, and a flexible region positioned proximal the distal region. A suture flange may be disposed about the cannula distal the flexible region. The flexible region can be bent and retains its bent configuration until a positive force is applied.

33 Claims, 5 Drawing Sheets

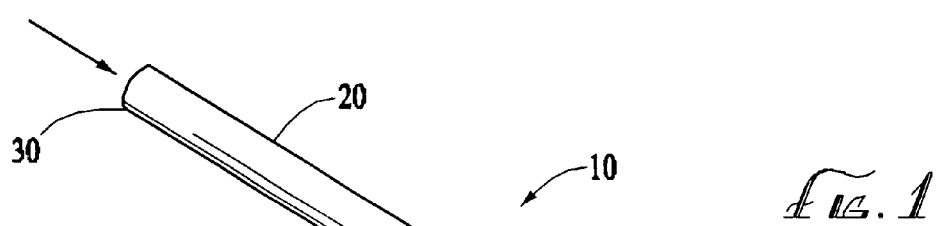
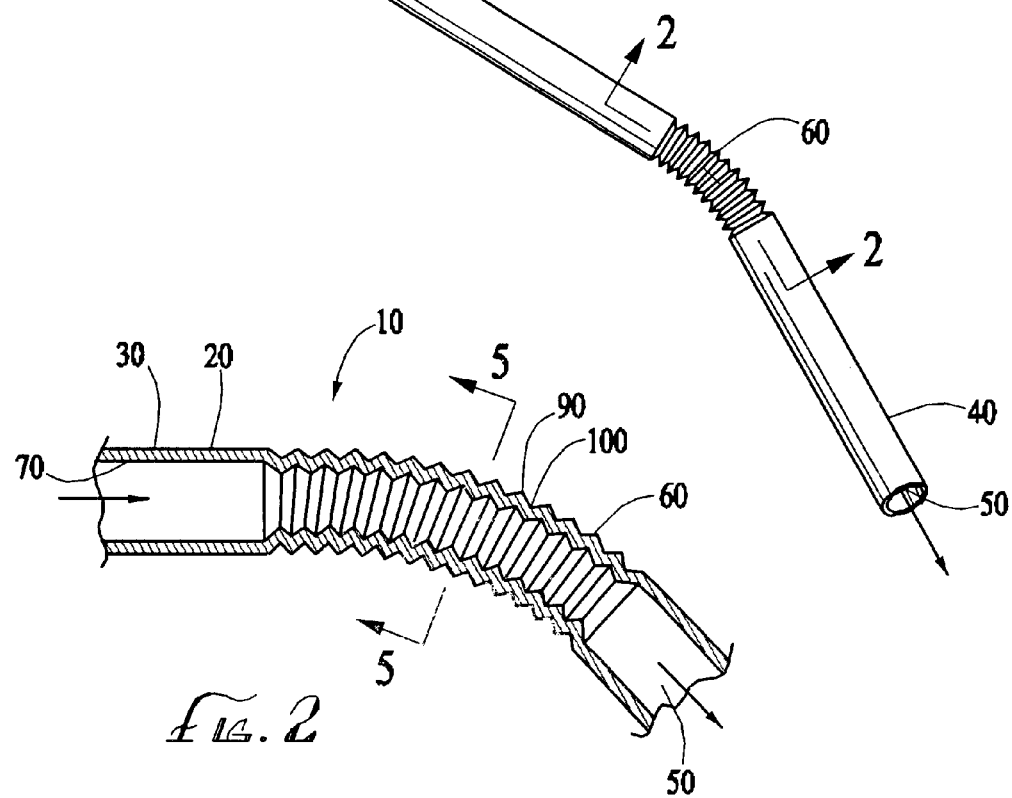
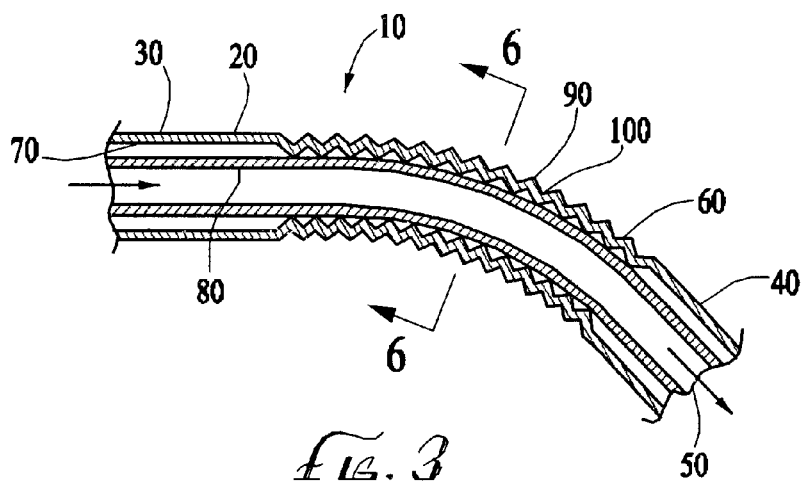

BENDABLE SHAPE-RETAINING CANNULA

FIELD OF THE INVENTION

The present invention relates generally to a cannula for temporary placement in a patient's vascular system during surgery. More particularly, the invention relates to arterial and venous cannulas which can be employed to deliver blood from or to a bypass-oxygenator machine during cardiopulmonary bypass, or to deliver cardioplegia solution to the heart.

BACKGROUND OF THE INVENTION

During various cardiothoracic surgeries, including cornary artery bypass grafting, heart valve replacement, septal defect repairs, and thoracic aortic aneurysm repair, cardiopulmonary bypass is often used to temporarily perform the function of the heart and lung while the surgeon repairs the diseased coronary artery, myocardium, valves, or aorta. Cardiopulmonary bypass is usually achieved by cannulation of the right atrium (where a venous return catheter carries deoxygenated blood from the right atrium to the bypass-oxygenator) and the aorta or femoral artery (where an arterial cannula returns the oxygenated blood from the bypass-oxygenator to the aorta).

Once cardiopulmany bypass is initiated, cardiac arrest is achieved by infusing cardioplegia solution into the coronary arteries to protect the myocardium and therefore reduce cardiac oxygen demand. Cardioplegia solution is often delivered through an aortic root cannula.

The cannulas that are currently available for arterial or venous cannulation, however, are cumbersome because of their rigid straight configuration, often interfering with the surgeon's hands and instruments, slowing the operation. A need therefore exists for space-conserving cannula devices and methods which provide delivery of blood from or to a bypass-oxygenator machine and delivery of cardioplegia solution to the heart during cardiothoracic surgery.

SUMMARY OF THE INVENTION

The present invention provides a bendable shape-retaining cannula which accommodates arterial blood flow from a bypass-oxygenator machine, venous blood flow to a bypass-oxygenator machine, and/or delivers cardioplegia solution for cardiac arrest during cardiothoracic surgeries. More specifically, the invention provides a space-conserving cannula which is less prone to interfere with a surgeon's field of operation.

In one embodiment, the bendable shape-retaining cannula comprises a tubular member having a proximal region adapted for attachment to a bypass-oxygenator machine, a distal region adapted to enter a blood vessel or heart chamber, a lumen extending therebetween, and a flexible region defined along a portion of the longitudinal axis. A suture flange is disposed about the cannula distal the flexible region and proximal the distal opening. The cannula is bendable because the flexible region comprises an accordion that can be bent by offsetting the proximal region relative to the distal region. Furthermore, the bend in the flexible region is retained until a positive force is applied to reorient the cannula. In certain embodiments, the cannula may also include an inner lining which either runs along its entire length or is limited to the flexible region so that blood or fluid flowing through the cannula does not encounter turbulance as it passes against the ridges of the flexible region. The inner lining thus provides smooth flow of blood or fluid through the cannula.

In another embodiment, the cannula may have a balloon occluder mounted on its distal region and communicating with a second lumen of the cannula. The balloon occluder provides aortic occlusion, thereby isolating the heart and the coronary blood vessels from the peripheral vascular system for cardiopulmonary bypass.

In another embodiment, the distal region of the cannula may have at least one venous drainage port. When the cannula is inserted in the right atrium, the superior vena cave, or the inferior vena cava, deoxgenated blood can be withdrawn through the lumen of the cannula to a bypass-oxygenator machine.

In still another embodiment, the cannula may have a filter as described in Barbut et al., U.S. Pat. No. 5,769,816, incorporated herein by reference, mounted on its distal region to entrap embolic material, such as thrombus, atheromatous plaque, fat, and tissue debris, from the aorta or cardiac chamber during cardiothoracic surgeries. The filter therefore reduces a patient's risk of perioperative stroke.

The present invention also provides methods for cannulation of a body tissue, more particularly a patient's blood vessel or heart chamber during cardiothoracic surgeries, including coronary artery bypass grafting, heart valve repair, septal defect repair, aneurysm repair, and correction of congenital defects. After an incision is made on a patient's aorta, for example, the distal end of the bendable and shape-retaining cannula described above is introduced into the aorta such that part of the flexible region of the cannula remains outside of the aorta. Oxygenated blood from a bypass-oxygenator is delivered through the proximal end to the lumen of the cannula, and then to the aorta. The cannula is bent by offsetting its proximal region relative to the distal region, thus moving the proximal end of the cannula away from interfering with the surgeon. The cannula can be secured to the aorta by placing sutures between the suture flange and the aorta. The cannula may also be inserted in the aorta to deliver cardioplegia solution to the heart to achieve cardiac arrest. Similarly, the cannula can be inserted into the right atrium, the inferior vena cava, or the superior vena cava to carry deoxgenated blood through the venous drainage ports and the lumen of the cannula to a bypass-oxygenator machine.

The present invention therefore provides a cannula which is bendable and retains a bent conformation until a positive force is applied to change the conformation. The invention also provides methods for cannulating a blood vessel or heart chamber using a bendable cannula that can be adjusted to conserve space while operatively maintained within the blood vessel or heart.

BRIEF DESCRIPTION OF THE DRAWINGS

Reference is next made to a brief description of the drawings, which are intended to illustrate bendable shape-retaining cannulas for use herein. The drawings and detailed description which follow are intended to be merely illustrative and are not intended to limit the scope of the invention as set forth in the appended claims.

FIG. 1 depicts a three-dimensional view of a bendable shape-retaining cannula according to one embodiment.

FIG. 2 depicts a longitudinal view of the bendable shape-retaining cannula shown in FIG. 1.

FIG. 3 depicts a longitudinal view of a bendable shape-retaining cannula according to another embodiment in which an impermeable inner lining runs along the entire length of the lumen of the cannula.

DETAILED DESCRIPTION OF THE INVENTION

Figure 9:
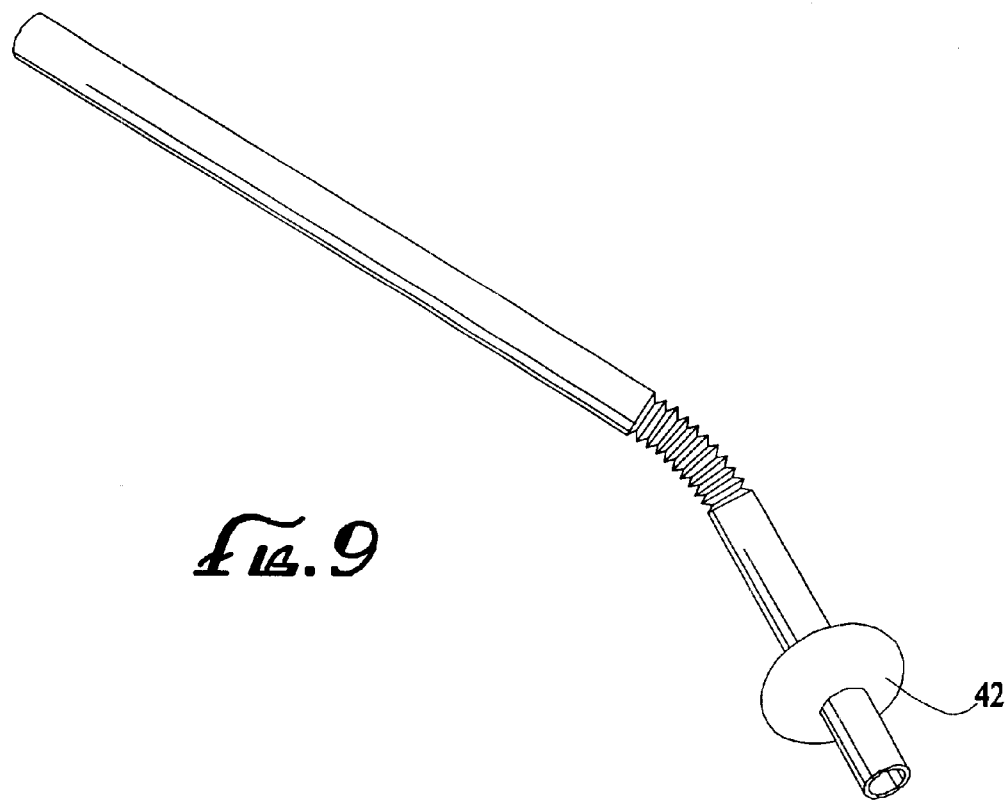
Figure 10:
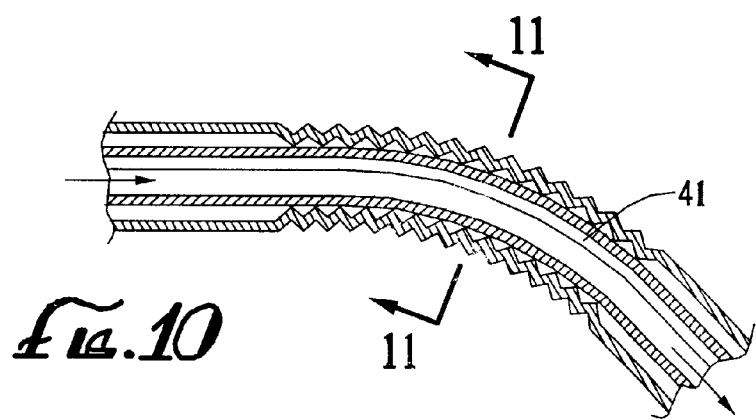
Figure 11:
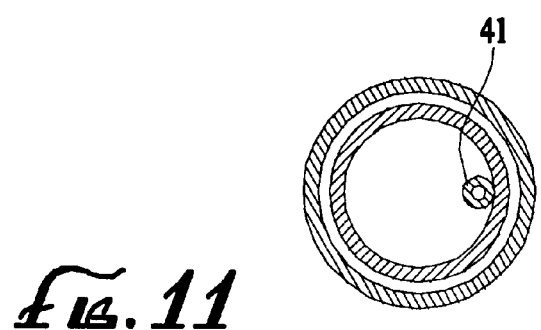
Figure 12:
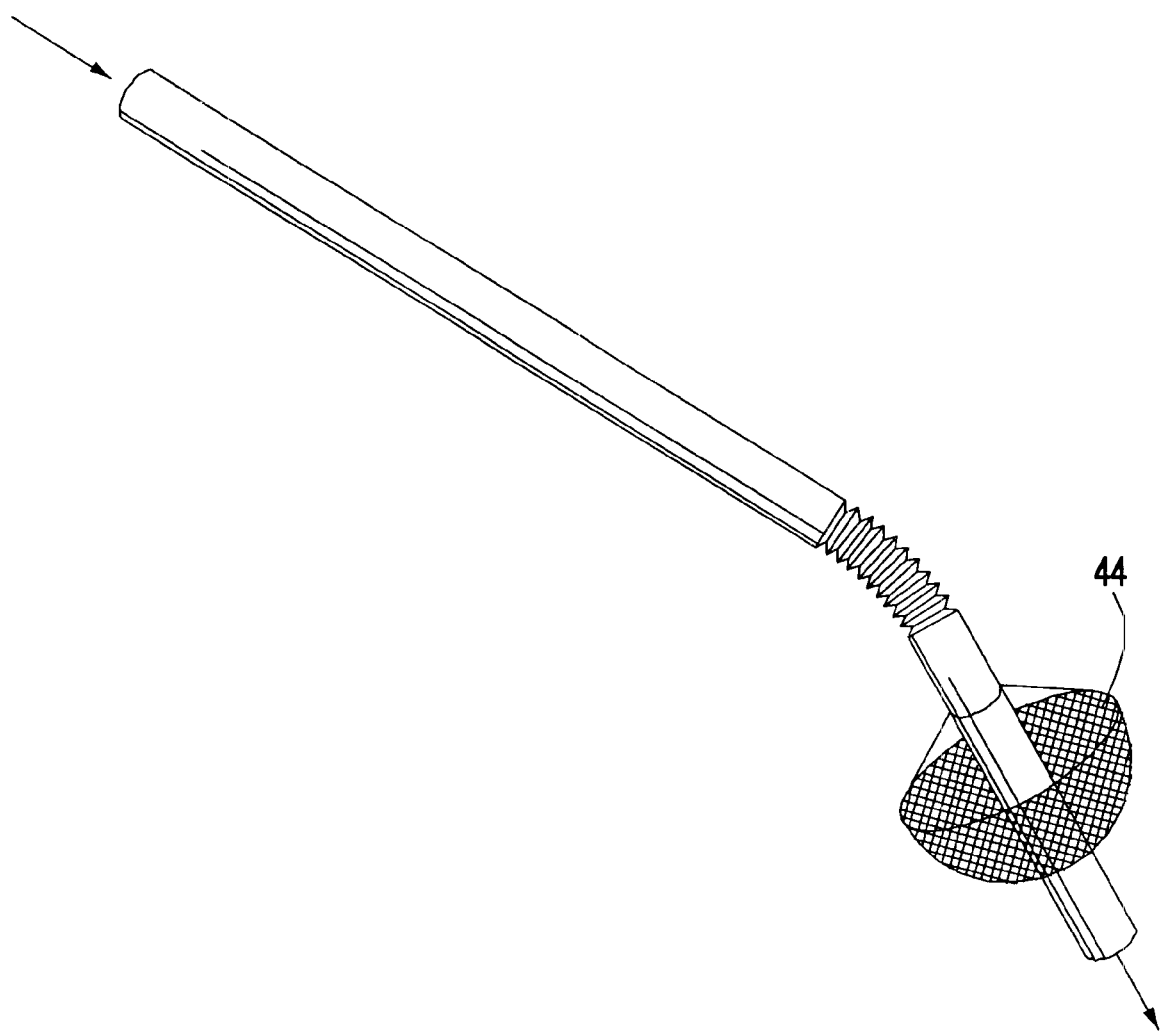

Referring more particularly to the drawings, FIG. 1 depicts a first embodiment of the bendable shape-retaining cannula for use herein. Cannula 10 comprises tubular member 20 having proximal region 30 adapted to receive blood from a bypass-oxygenator machine, distal region 40 adapted to enter an artery, lumen 50, and flexible region 60 defined along a portion of the longitudinal axis. Flexible region 60 is proximal of distal region 40. Flexible region 60 can be bent in any direction by offsetting proximal region 30 relative to distal region 40 so that the longitudinal axis of the proximal region is angled relative to the longitudinal axis of the distal region. Flexible region 60 retains its bent conformation until a positive force is applied. In another embodiment as shown in FIG. 9, the cannula has an expandable balloon occluder 42 mounted on its distal region and communicating with a second lumen 41 of the cannula shown in FIGS. 10 and 11. In still another embodiment as shown in FIG. 12, the cannula has an expandable filter 44 as described in Barbut et al. U.S. Pat. No. 5,769,816, incorporated herein by reference, mounted on its distal region to entrap embolic material, such as thrombus, atheromatous plaque, fat, and tissue debris, from the aorta or cardiac chamber during cardiothoracic surgeries.

Figures 5, 6:
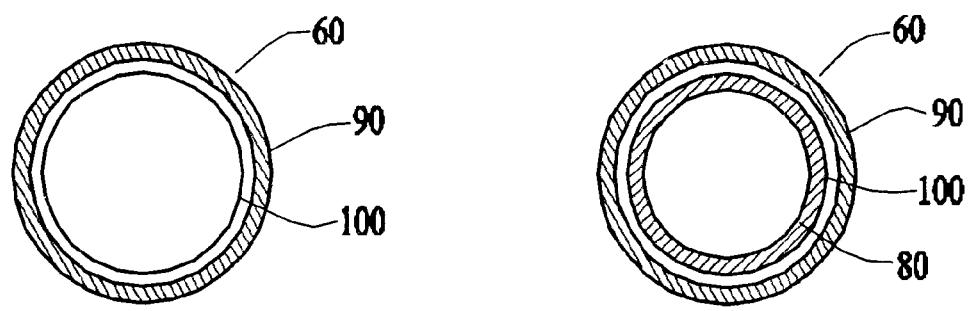
FIG. 5 depicts a cross-sectional view through section 5—5 of the cannula shown in FIG. 2.
FIG. 6 depicts a cross-sectional view through section 6—6 is a longitudinal view of a bendable shape-retaining cannula according to another embodiment.

FIG. 2 shows a longitudinal view of the bendable shape-retaining cannula 10 depicted in FIG. 1. Cannula 10 is shown in a bent conformation and can be bent in any direction at flexible region 60. Flexible region 60 will bend when a force is applied on proximal region 30 and will retain that bent conformation until another force is applied on proximal region 30. Tubular member 20 of cannula 10 includes inner wall 70 which is generally straight both proximal and distal to flexible region 60. However, within flexible region 60, inner wall 70 is corrugated. FIG. 5 depicts a cross-sectional view of the corrugation in flexible region 60, including vertex 90 extending away from the lumen of bendable shape-retaining cannula 10, and vertex 100 extending into the lumen of cannula 10, the two apexes forming a segment of the corrugation.

FIG. 3 shows another embodiment of the bendable shape-retaining cannula. Cannula 10 has a tubular member 20 having proximal region 30 adapted to receive blood from a bypass-oxygenator machine, distal region 40 adapted to enter a blood vessel or heart chamber, lumen 50, flexible region 60, and impermeable inner lining 80 running along inner wall 70 through the entire length of lumen 50. Lining 80 provides a smooth surface for blood or fluid to flow through the lumen of the corrugated flexible region 60, thereby reducing turbulent flow. Lining 80 can be secured to inner wall 70 by any one of (1) intermittent attachment to the inner wall with clips or adhesive material, and (2) continuous adhesion to the inner wall, except in the flexible region where the lining contacts the inner wall only at the vertices of the ridges forming the corrugation. FIG. 6 depicts a cross-sectional view of the corrugation in flexible region 60, including vertex 90 extending away from the lumen of the cannula 10, and vertex 100 extending toward the cannula lumen, the two vertices forming part of the corrugation. FIG. 5 also shows lining 80 fixed to vertex 100 extending toward the lumen of the bendable shape-retaining cannula.

Figure 4:
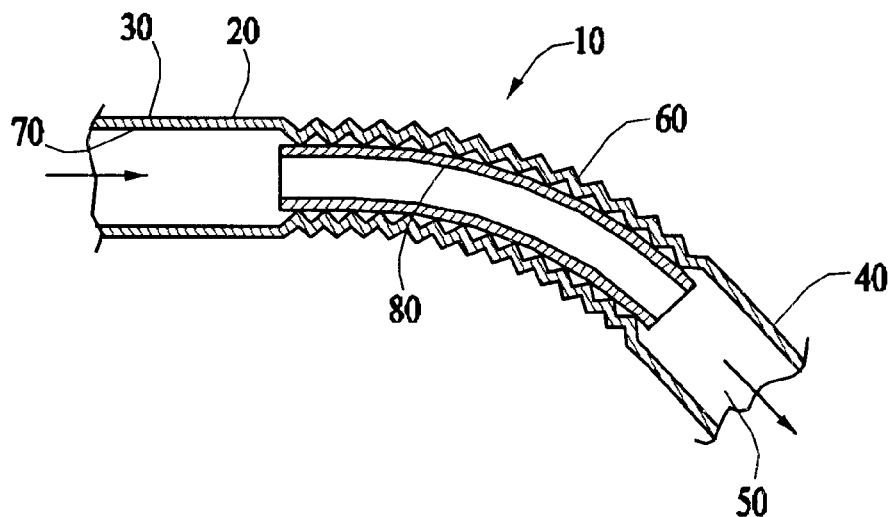
FIG. 4 depicts a longitudinal view of a shape-retaining cannula according to another embodiment, in which the flexible portion of the cannula has an impermeable inner linning.

FIG. 4 shows another embodiment of the bendable shape-retaining cannula. This embodiment is identical to the embodiment depicted in FIG. 3 except lining 80 does not run the entire length of the cannula. Instead, lining 80 runs alongside inner wall 70, only in the area of flexible region 60. This embodiment also prevents disruption of blood flow. The lining may be secured to wall 70 in the area of flexible region 60 by fixing it to the vertices of the ridges forming the corrugation.

Figure 7:
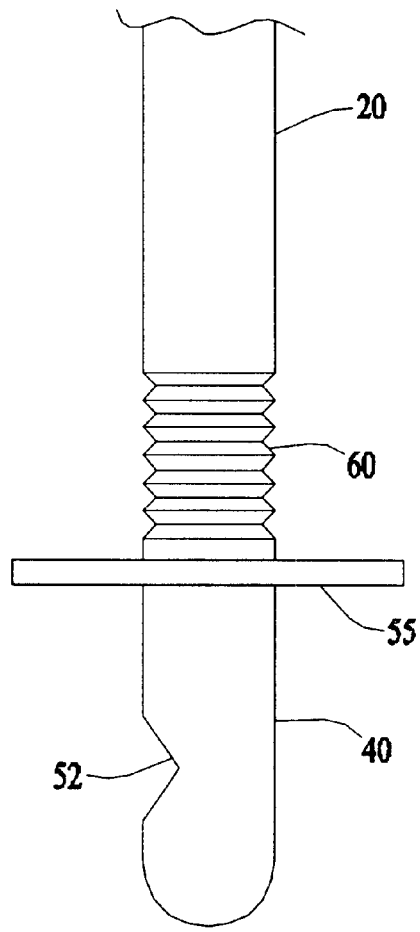
FIG. 7 depicts a distal region of the cannula having a suture flange.

FIG. 7 depicts a distal region of the bendable shape-retaining cannula having suture flange 55 distal flexible region 60. In use, distal region 20 of the cannula is inserted into a patient's aorta, and blood from a bypass-oxygenator machine is delivered to the aorta through opening 52. Sutures can be placed between suture flange 55 and the aorta to secure the cannula onto the aorta. The cannula is then bent at region 60 to position the cannula away from the field of operation after cardiopulmonary bypass is initiated. Suture flange 55 may be slideable on the distal region of the cannula so that the segment of the distal region inside the aorta may be adjusted for changing surgical conditions. A flow diffuser may also be included in the distal region.

Figure 8:
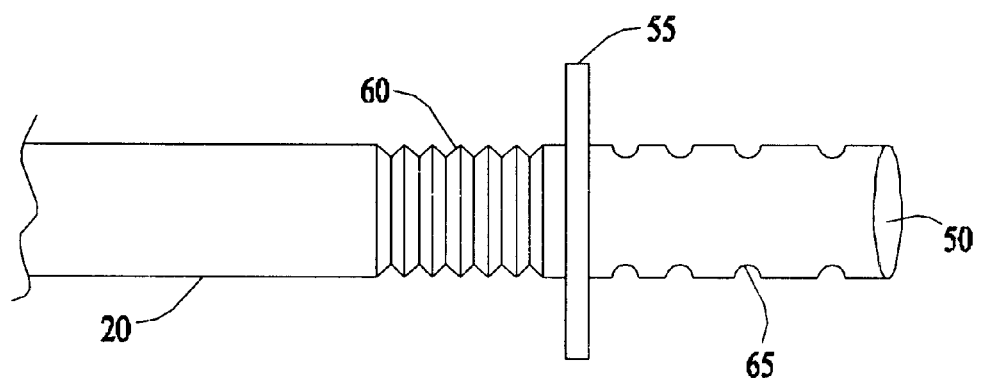
FIG. 8 depicts a distal region of the cannula having at least one venous drainage port.

FIG. 8 depicts another embodiment of the bendable shape-retaining cannula having one or more venous drainage ports 65 at distal region 20. In use, distal region 20 of the cannula is inserted into a patient's right atrium, superior vena cava, or inferior vena cava to provide drainage of deoxygented blood to a bypass-oxygenator machine. Sutures may be placed between suture flange 55 and the right atrium or the great vessels to secure the cannula in place. The cannula is bent by the surgeon at region 60 to move the cannula away from the field of surgery. Venous blood is drained through venous drainage ports 65 and lumen 50 to a bypass-oxygenator machine.

The length of the lumen 50 will generally be between 5 and 45 centimeters, preferably approximately 30 centimeters (cm). The cross-sectional diameter of lumen 50 will generally be in the range of 0.3 cm to 2 cm, preferably approximately 1 cm. The length of corrugation in the flexible region 60 will be between 1 cm to 5 cm, preferably approximately 2 cm. The foregoing ranges are set forth solely for the purpose of illustrating typical device dimensions. The actual dimensions of a device constructed according to the principles of the present invention may obviously vary outside of the listed ranges without departing from those basic principles.

In coronary artery bypass surgery, the bendable shape-retaining cannula may be inserted about 5 cm above the aortic valve into the ascending aorta for arterial cannnulation or into the right atrium, inferior vena cava, or superior vena cava for venous cannulation following sternotomy. When cardiopulmanoary bypass is initiated, the aortic cannula carries oxygenated blood from the bypass-oxygenator machine to the aorta whereas the venous canula carries deoxygenated blood from the right atrium or the vena cava to the bypass-oxygenator machine. When cardiac arrest is required, the cannula may be inserted in the aortic root to deliver cardioplegia solution upstream to the heart. The cannula may be left in place and bent by the surgeon to minimize interference, thus improving the working space and obviating the need for removal of the cannula during bypass surgery. The cannula is eventually removed after the patient is weaned from cardiopulmanary bypass and cardiac arrest is reversed. The bendable shape-retaining cannula can also be employed in a similar fashion disclosed above in surgeries including thoracic aneurysm repair, septal defects repair, and aortic or mitral valvular replacement when cardiopulmanary bypass and cardiac arrest are indicated.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A bendable cannula comprising:
   a unibody tubular member having a proximal region, a distal region adapted to enter a blood vessel or heart chamber, a lumen extending therebetween and communicating with a distal opening, an expandable impermeable occluder mounted on the distal region, and a flexible region defined along a portion of the longitudinal axis, the flexible region being proximal the distal region and comprising accordion pleats; and
   a suture flange disposed about the cannula distal the flexible region and proximal the distal opening, wherein the flexible region of the cannula can be bent by offsetting said proximal region relative to said distal region so that a longitudinal axis of the proximal region is angled relative to the longitudinal axis of the distal region, and wherein the bend in the flexible region is maintained.

2. The cannula of claim 1, further comprising a generally cylindrical lining which extends along the lumen in the area of the flexible region.

3. The cannula of claim 2, wherein the lining is secured to the inner wall of the arterial cannula with adhesive.

4. The cannula of claim 1, wherein the suture flange is slideable.

5. The cannula of claim 1, wherein the proximal region of the tubular member is adapted for attachment to a bypass-oxygenator machine.

6. The cannula of claim 1, wherein the distal region of the tubular member further comprises at least one venous drainage port.

7. The cannula of claim 1, wherein the cannula further comprises a second lumen, and wherein said second lumen communicates with the expandable occluder.

8. The cannula of claim 1, wherein the expandable occluder is a balloon occluder.

9. A method for cannulation of a body tissue, comprising the steps of:
   providing a cannula comprising a unibody tubular member having a proximal region, a distal region, a lumen therebetween, an expandable impermeable occluder mounted on the distal region, and a flexible region comprising accordion pleats defined along a portion of the cannula, the flexible region being proximal the distal region;
   making an incision on an aorta;
   introducing the distal region of the cannula through the incision into the aorta;
   infusing fluid through the cannula;
   bending the flexible region by offsetting the proximal region relative to the distal region so that a longitudinal axis of the proximal region is angled relative to a longitudinal axis of the distal region, wherein the bend in the flexible region is retained; and
   expanding the occluder.

10. The method of claim 9, wherein the cannula further comprises a generally cylindrical lining which extends along the lumen.

11. The method of claim 10, wherein the lining extends along the lumen in the area of the flexible region.

12. The method of claim 10, wherein the proximal region of the tubular member is adapted for attachment to a bypass-oxygenator machine.

13. The method of claim 9, wherein the cannula further comprises a suture flange disposed distal the flexible region.

14. The method of claim 9, wherein the fluid is blood from a bypass-oxygenator machine.

15. The method of claim 9, wherein the fluid is cardioplegia solution.

16. The method of claim 9, wherein the suture flange is slidably mounted on the distal region of the tubular member.

17. The method of claim 9, wherein the distal region of the tubular member comprises at least one venous drainage port.

18. The method of claim 9, further comprising the step of performing coronary artery bypass grafting surgery.

19. The method of claim 9, wherein the expandable occluder is a balloon occluder.

20. The method of claim 9, wherein the occluder is expanded before the step of infusing fluid through the cannula.

21. The method of claim 9, wherein the occluder is expanded before the step of bending the flexible region.

22. A method for cannulation of a body tissue, comprising the steps of:
   providing a cannula comprising a unibody tubular member having a proximal region, a distal region, a lumen therebetween, an expandable filter mounted on the distal region, and a flexible region comprising accordion pleats defined along a portion of the cannula, the flexible region being proximal of the distal region;
   making an incision in an aorta;
   introducing the distal region of the cannula into the aorta;
   infusing fluid through the cannula;
   bending the flexible region by offsetting the proximal region relative to the distal region so that a longitudinal axis of the proximal region is angled relative to a longitudinal axis of the distal region, wherein the bend in the flexible region is retained; and
   expanding the filter.

23. The method of claim 22, wherein the cannula further comprises a generally cylindrical lining which extends along the lumen.

24. The method of claim 23, wherein the lining extends along the lumen in the area of the flexible region.

25. The method of claim 22, wherein the cannula further comprises a suture flange disposed distal the flexible region.

26. The method of claim 25, wherein the suture flange is slideably mounted on the distal region of the tubular member.

27. The method of claim 22, wherein the fluid is blood from a bypass-oxygenator machine.

28. The method of claim 22, wherein the fluid is cardioplegia solution.

29. The method of claim 22, wherein the distal region of the tubular member further comprises at least one venous drainage port.

30. The method of claim 22, wherein the proximal region of the tubular member is adapted for attachment to a bypass-oxygenator machine.

31. The method of claim 22, further comprising the step of performing coronary artery bypass grafting surgery.

32. The method of claim 22, wherein the filter is expanded before the step of infusing fluid through the cannula.

33. The method of claim 22, wherein the filter is expanded before the step of bending the flexible region.

* * * * *